(12) United States Patent
Kanahara

(10) Patent No.: US 7,726,180 B2
(45) Date of Patent: Jun. 1, 2010

(54) FLOAT AND LIQUID CONTAINER USING THE FLOAT, METHOD FOR PREVENTING MALFUNCTION OF PROBE IN AUTOMATIC ANALYZER, AND EXAMINATION METHOD USING AUTOMATIC ANALYZER

(75) Inventor: Masaaki Kanahara, Kurume (JP)

(73) Assignee: Kurume University, Kurume-shi (JP)

( * ) Notice: Subject to any disclaimer, the term of this patent is extended or adjusted under 35 U.S.C. 154(b) by 258 days.

(21) Appl. No.: 11/909,918

(22) PCT Filed: Mar. 27, 2006

(86) PCT No.: PCT/JP2006/306094

§ 371 (c)(1),
(2), (4) Date: Sep. 27, 2007

(87) PCT Pub. No.: WO2006/104076

PCT Pub. Date: Oct. 5, 2006

(65) Prior Publication Data

US 2009/0139326 A1 Jun. 4, 2009

(30) Foreign Application Priority Data

Mar. 28, 2005 (JP) ............................. 2005-092528

(51) Int. Cl.
*G01N 35/00* (2006.01)
*G01F 23/00* (2006.01)
*B63B 35/44* (2006.01)
*B63B 22/18* (2006.01)

(52) U.S. Cl. .................... 73/64.56; 73/306; 73/291; 114/267; 441/21

(58) Field of Classification Search ................ 73/305, 73/309, 306, 322.5, 291, 64.56, 864.91, 863.81, 73/864.21, 864.81; 441/21–22, 136; 114/264, 114/267
See application file for complete search history.

(56) References Cited

U.S. PATENT DOCUMENTS 1,992,502 A * 2/1935 Palm ...................... 73/322.5 X (Continued)

FOREIGN PATENT DOCUMENTS

EP 1 106 252 A2 6/2001

(Continued)

OTHER PUBLICATIONS

English Translation of JP 2000-214171, Apr. 8, 2000.*

*Primary Examiner*—Thomas P Noland
(74) *Attorney, Agent, or Firm*—Edwards Angell Palmer & Dodge LLP

(57) ABSTRACT

In a liquid container used in an automatic analyzer, a float that makes it possible to prevent liquid from making contact with a liquid collection opening of the liquid container to form a film thereon is provided. A float is floated on the liquid surface of a reagent placed in a reagent container for use with an automatic analyzer. The float is equipped with a float body and a required number of buoyancy adjusters. The float body is equipped with a liquid surface cover that covers substantially the entire liquid surface, and a side wall portion positioned so as to project beneath the liquid surface from the liquid surface cover. The side wall portion constitutes a device for the purpose of suppressing swaying motions of the liquid surface cover by making contact with or engaging an inner wall of the reagent container when the reagent sways.

15 Claims, 4 Drawing Sheets

U.S. PATENT DOCUMENTS

| | | | |
|---|---|---|---|
| RE25,236 E | * | 9/1962 | Davies et al. ............... 137/390 |
| 3,425,279 A | * | 2/1969 | Conkling et al. ......... 73/861.21 |
| 4,607,404 A | * | 8/1986 | Fraige ........................... 5/683 |
| 4,894,873 A | * | 1/1990 | Kiefer et al. .................... 4/497 |
| 5,299,456 A | * | 4/1994 | Steiner .................. 73/322.5 X |
| 6,409,528 B1 | | 6/2002 | Bodnar |
| 2002/0061542 A1 | * | 5/2002 | Rimm et al. ................ 435/7.21 |

FOREIGN PATENT DOCUMENTS

| | | | | |
|---|---|---|---|---|
| GB | 2149298 A | * | 6/1985 | |
| JP | 1981-138370 U | | 10/1981 | |
| JP | 57046123 A | * | 3/1982 | |
| JP | 1983-3936 U | | 1/1983 | |
| JP | 1-111656 A | | 1/1994 | |
| JP | 2000-214171 A | | 8/2000 | |
| JP | 2001-264316 A | | 9/2001 | |
| JP | 2005-83777 A | | 3/2005 | |

* cited by examiner

PRIOR ART

FLOAT AND LIQUID CONTAINER USING THE FLOAT, METHOD FOR PREVENTING MALFUNCTION OF PROBE IN AUTOMATIC ANALYZER, AND EXAMINATION METHOD USING AUTOMATIC ANALYZER

CROSS REFERENCE TO PRIOR RELATED APPLICATIONS

This application is a U.S. national phase application under 35 U.S.C. §371 of International Patent Application No. PCT/JP2006/306094, filed Mar. 27, 2006, and claims priority to Japanese Patent Application No. 2005-092528, filed Mar. 28, 2005, both of which are incorporated by reference herein. The International Application was published in Japanese on Oct. 5, 2006 as International Publication No. WO 2006/104076 A1 under PCT Article 21(2).

FIELD OF THE INVENTION

The present invention relates to a float and a liquid container that uses the float, a method for preventing malfunction of a probe in an automatic analyzer, and an examination method using an automatic analyzer. More specifically, the present invention relates to a float, and a liquid container and the like equipped with the float, made capable of preventing a film from being formed when a liquid such as a reagent comes into contact with a liquid collection opening of a liquid container used in an automatic analyzer.

BACKGROUND OF THE INVENTION

In blood tests such as a blood coagulation test, an automatic analyzer that automatically analyzes blood is used. Various solutions are used as reagents in a blood test. A reagent is placed into a designated reagent container and housed inside an automatic analyzer. The reagent is then collected with a thin pipe-shaped collection tube called a probe and dispensed into a reaction container containing a blood sample, and analysis is performed.

By way of an explanation in further detail, as shown in FIG. 4, for example, a plurality of reagent containers 2 are held on a turntable 4 inside an automatic analyzer. As shown in FIG. 5, at the top part of the reagent container 2, a reagent collection opening 221 into which a probe 5 can be inserted is open. The diameter of the reagent collection opening 221 is small, which prevents deterioration of the reagent as a result of oxidation and the like caused by contact with air.

The probe 5 is mounted on the tip of an arm 51. The turntable 4 rotates so as to position a desired reagent container 2 directly underneath the probe 5. Then, through vertical and rotational motions of the arm 51, the probe 5 is made to move between the reagent container 2 and a reaction container (not shown in the figure). A liquid-level sensor is mounted on the tip of the probe 5 and is set up so that even if the height of the liquid surface of the reagent to be collected changes, the tip of the probe 5 can be inserted beneath the liquid surface.

In order to increase the examination processing speed, the turntable 4 rotates not only in one direction but in both left and right directions, quickly and in small movements. Accordingly, as shown in FIG. 5, if the liquid level of the reagent in the reagent container 2 is high, the reagent may, in some cases, splash up and contact the reagent collection opening 221 to form a thin film 6. In such a case, the liquid-level sensor at the tip of the probe 5 will mistakenly detect the film as the liquid surface, and the collection operation will be performed in midair where the reagent does not exist. As a result, even if the probe 5 moves to the reaction container, the reagent will not be dispensed and an incorrect examination value will be obtained.

In order to prevent this sort of mistake from occurring, it will be necessary to make the amount of reagent provided, for example, not exceed one-half the volume of the reagent container so that the reagent does not splash up. But, if the amount of reagent provided is small, the frequency with which to replenish the reagent will necessarily increase. However, since many varieties of reagents are used in blood tests, it is preferable to keep the frequency of replenishment low in order to prevent human-made errors such as mistaking a reagent to be replenished.

Also, when the amount of reagent provided is reduced, an increase in the area of contact with air per unit volume of reagent leads to the drawback of facilitating reagent deterioration. Therefore, it is preferable to have a large amount of reagent provided in the reagent container 2, but for that purpose a means to prevent the reagent from splashing up to the reagent collection opening 221 will be necessary.

Japanese Unexamined Patent Application Publication No. 2000-214171 (JP '171) proposes, in FIG. 1 on page 9, a solution stabilization member that floats on the liquid surface within a reagent container so as to prevent oxidation and the like caused by contact with air and ensure obtaining a stable quality of the reagent.

SUMMARY OF THE INVENTION

However, even if the member described in JP '171 is able to ensure obtaining a stable quality of the reagent, it is difficult as mentioned above to prevent the reagent from splashing up and making contact with the reagent collection opening 221.

That is, the solution stabilization member described in JP '171 is formed in a thin plate shape from a foam material such as polyethylene foam. Therefore, even if the solution stabilization member 7 is used in the reagent container 2 shown in FIG. 5, as hypothetically shown in FIG. 6, the solution stabilization member 7 will also tilt to the left and right together with the liquid surface when the reagent container 2 sways horizontally. As a result, as shown in FIG. 6, the reagent moves along the inner wall 211 to splash up momentarily through the gap formed between the inner wall 211 of the reagent container 2 and the solution stabilization member 7, making contact with the reagent collection opening 221 to form a film 6.

Even in cases as described above in which an incorrect examination value is obtained, there will essentially be no problem if a system is in place whereby a technician in charge of the examination checks the results and performs a re-examination. Nevertheless, since the results of a blood test provide important data for judgment when a doctor prescribes clinical treatment to a patient, under no circumstances should an incorrect test result be reported. Therefore, any source of concern that may lead an automatic analyzer to produce an incorrect examination result should be eliminated, even if it is at a stage prior to the examination results being reported to the doctor.

It is therefore an object of the present invention to provide a float, and a liquid container equipped with the float, made capable of preventing a film from being formed when liquid comes into contact with a liquid collection opening of a liquid container used in an automatic analyzer.

Another object of the present invention is to provide a method for preventing malfunction of a probe in an automatic analyzer by preventing a probe equipped with a liquid-level sensor in an automatic analyzer from mistakenly detecting a film formed on a liquid collection opening of a liquid container as a liquid surface.

Yet another object of the present invention is to provide an examination method using an automatic analyzer that is made capable of preventing obtaining incorrect examination values by preventing malfunction of a probe in the automatic analyzer.

The present invention institutes the following means to achieve the objects stated above.

To aid in understanding the explanation of the operation given further below, reference numerals used in the drawings are parenthesized when cited, but each of the constituent elements is not limited to the features described in the drawings.

One aspect of the invention is a float for the purpose of floating on a liquid placed in a liquid container (2) for use with an automatic analyzer, wherein the float is characterized by being equipped with: a liquid surface cover (11) capable of covering substantially the entire liquid surface and provided with an opening (111) for the purpose of collecting the liquid; and a device (12) for suppressing swaying motions that makes contact with or engages an inner wall (211) of the liquid container (2) when the liquid sways so as to suppress swaying motions of the above-mentioned liquid surface cover (11).

Another aspect of the invention is a float for the purpose of floating on a liquid placed in a liquid container (2) for use with an automatic analyzer, wherein the float is characterized by being equipped with: a liquid surface cover (11) capable of covering substantially the entire liquid surface and provided with an opening (111) for the purpose of collecting the liquid; and a device (12) for suppressing liquid force, positioned so as to project beneath the liquid surface and constituted so as to suppress the force of the liquid that moves toward an inner wall (211) of the liquid container (2) when the liquid sways.

Another aspect of the invention is the float as described above, characterized in that concavities and convexities (121) are provided on a side that makes contact with the inner wall (211) of the liquid container (2).

Another aspect of the invention is the float as described above, characterized in that it is provided with a means (3) for adjusting buoyancy.

Another aspect of the invention is a liquid container equipped with a float, characterized in that it is provided with the float (1) as described above, and the liquid container (2).

Another aspect of the invention is a method for preventing malfunction of a probe equipped with a liquid-level sensor in an automatic analyzer wherein a film formed on a liquid collection opening of a liquid container is mistakenly detected as the surface of a liquid, the method for preventing malfunction of a probe in an automatic analyzer being characterized by floating the float as described above on the liquid in the liquid container so as to prevent the liquid from making contact with the above-mentioned liquid collection opening so that a film is not formed.

Another aspect of the invention is an examination method using an automatic analyzer that is provided with a liquid container disposed on a movable mounting unit, collects the liquid inside the liquid container by means of a probe equipped with a liquid-level sensor, and performs analyses, the examination method using an automatic analyzer being characterized by floating the float as described above on the liquid in the liquid container so as to perform examination in a state wherein the liquid is prevented from making contact with a liquid collection opening of the liquid container.

The float (1) of the present invention operates as follows.

The float (1) is floated on the liquid surface of a liquid placed in the liquid container (2) for use with an automatic analyzer. In cases in which the float (1) has the means (3) for adjusting buoyancy, buoyancy is adjusted according to the specific gravity and viscosity of the liquid so that the float (1) does not sink beneath the liquid surface.

By floating the float (1) on the liquid surface, the area of contact between the liquid surface and air can be reduced. The liquid container (2), in which the float (1) is floating, is mounted onto a movable mounting unit (4) such as a turntable inside the automatic analyzer, and the analysis is commenced.

The movable mounting unit (4) rotates so that the desired liquid container (2) is positioned directly underneath the probe (5). Then an arm (51) is lowered, and the probe (5) is inserted through the liquid collection opening (221) of the liquid container (2). The probe (5) is passed through an opening (111) in the float (1) and inserted beneath the liquid surface, and the liquid is collected. After collection, the liquid is dispensed into a reaction container containing a test specimen such as blood, and analysis is performed.

Although the liquid container (2) sways horizontally due to the movement of the movable mounting unit (4), the float (1), by acting as described below, prevents the liquid from making contact with the liquid collection opening (221).

That is, even if the liquid container (2) sways horizontally, swaying and tilting of the liquid surface are prevented or reduced since a liquid surface cover (11) of the float (1) covers substantially the entire liquid surface.

Furthermore, differing from a conventional solution stabilization member (7) (see FIG. 6) that ends up swaying together with the liquid surface when the liquid container (2) sways horizontally, in the present invention, a device (12) of the liquid surface cover (11) for suppressing swaying motions makes contact with or engages the inner wall (211) of the liquid container (2) so as to suppress swaying motions of the liquid surface cover (11). This prevents the formation of a gap between the inner wall (221) and the liquid surface cover (11), through which liquid may move along the inner wall (211) to splash up. Thus, it is possible to prevent the liquid from making contact with the liquid collection opening (221) of the liquid container (2) to form a film (6).

Also, in cases of a liquid surface cover (11) provided with a device (12) for suppressing liquid force, positioned so as to project beneath the liquid surface, the device (12) for suppressing liquid force suppresses the force of the liquid moving toward the inner wall (211) of the liquid container (2). This prevents the formation of a gap between the inner wall (211) and the liquid surface cover (11), through which liquid that collides with the inner wall (211) may splash up. Thus, it is possible to prevent the liquid from making contact with the liquid collection opening (221) of the liquid container (2) to form a film (6).

For a float provided with concavities and convexities (121) on the side that makes contact with the inner wall (211) of the liquid container (2), these concavities and convexities (121) reduce the contact area in cases in which the float (1) and the inner wall (211) come into contact. As a result, the float (1) moves up and down smoothly in accordance with changes in the height of the liquid surface. Also, the reduction of contact area prevents the float (1) from becoming stuck to the inner wall (211) of the liquid container (2).

The present invention is provided with the constitution described above and some of its effects are as follows.

According to the present invention, even in cases in which the liquid container, for example, sways horizontally, a device of the float for suppressing swaying motions makes contact with or engages the inner wall of the liquid container, thereby suppressing swaying motions of the liquid surface cover that covers substantially the entire liquid surface. Thus, formation of a gap between the inner wall and the liquid surface cover, through which liquid may move along the inner wall to splash up, is prevented. Accordingly, it is possible to prevent the liquid from making contact with the liquid collection opening of the liquid container to form a film. Consequently, it is possible to prevent the occurrence of incorrect examination results due to malfunction of a probe equipped with a liquid-level sensor.

Also, according to the present invention, even in cases in which the liquid container, for example, sways horizontally, a device of the float for suppressing liquid force, positioned so as to project beneath the liquid surface, suppresses the force of the liquid moving toward the inner wall of the liquid container. This makes it possible to prevent the liquid from forcefully colliding with the inner wall to splash up. Thus, similarly to the case described above, the liquid is prevented from making contact with the liquid collection opening of the liquid container to form a film, and it is possible to prevent the occurrence of incorrect examination results due to malfunction of a probe equipped with a liquid-level sensor.

For a float provided with concavities and convexities on the side that makes contact with the inner wall of the liquid container, the area of contact in cases in which the float and the inner wall make contact can be reduced. As a result, the float is able to move up and down smoothly in accordance with changes in the height of the liquid surface, and the liquid surface can be covered continuously with the liquid surface cover. Also, the reduction of contact area prevents the float from becoming stuck to the inner wall of the container body, and makes it possible to prevent the float from swaying with respect to the inner wall.

For a float provided with a means for adjusting buoyancy, even if the specific gravity and viscosity of the liquid stored in the liquid container change, the buoyancy of the float can be adjusted to an optimal state so that the float does not sink beneath the liquid surface.

According to a method for preventing malfunction of a probe in an automatic analyzer and an examination method that uses an automatic analyzer, as a result of the effects of the float described above, malfunction of a probe equipped with a liquid-level sensor is prevented, thus preventing the automatic analyzer from yielding incorrect examination results.

DETAILED DESCRIPTION OF THE INVENTION

Figure 1:
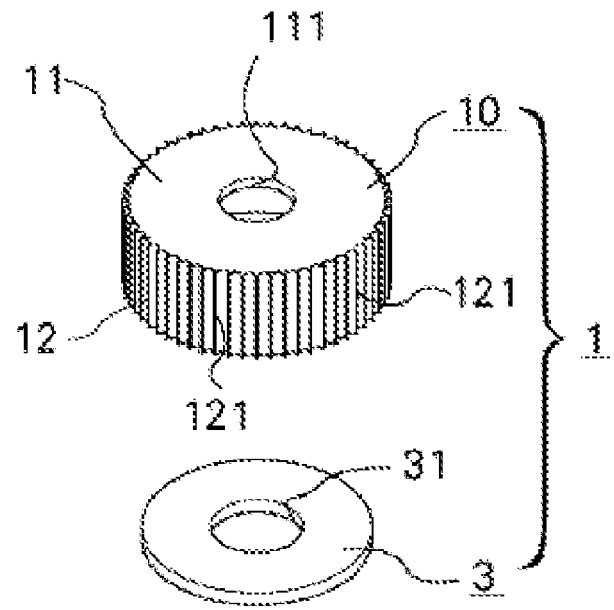
FIG. 1 is an exploded perspective view showing an embodiment of a float of the present invention.

Examples of test specimens subject to analysis by an automatic analyzer include body fluids sampled from humans or other mammals, i.e., blood, urine, ascitic fluid, pleural fluid, bone marrow fluid or bile, liquids for use in beverages, liquid foods, and the like.

The liquid container used in an automatic analyzer may be any publicly known container without any particular restrictions on the shape or size thereof. The float that floats on the liquid placed in the liquid container is designed appropriately in accordance with the shape and size of the liquid container. For example, there are liquid containers having a circular shape, a trapezoidal shape, an approximate fan shape, or a rectangular shape for the horizontal cross-sectional shape, and because the horizontal cross-sectional shape determines the shape of the liquid surface in the state of standing still, the liquid surface cover of a float can be each formed correspondingly into a circular shape, a trapezoidal shape, an approximate fan shape, or a rectangular shape, as seen in a plan view.

Examples of the float material include such synthetic resins as polypropylene and polyethylene. Also, depending on the type of liquid to be placed in the liquid container, materials having excellent chemical resistance may be used, and the same applies to the buoyancy adjuster to be described later.

For the device of the liquid surface cover for suppressing swaying motions, as long as it suppresses swaying motions of the liquid surface cover with respect to the inner wall of the liquid container, there are no particular restrictions on its shape, location of installation, or the like.

By way of a specific example, the device for suppressing swaying motions can be constituted at a side wall portion, a foot portion, a support portion, or the like. In cases in which the device for suppressing swaying motions is constituted at a side wall portion, the side wall portion may be provided so as to be continuous, or a required number of such devices may be provided at required intervals. The device for suppressing swaying motions may be provided to project, from the liquid surface cover, to beneath the liquid surface or to above the liquid surface, or to project both above and below the liquid surface. In particular, it is preferable to provide the device for suppressing swaying motions beneath the liquid surface since this also produces the effect of suppressing the force of the liquid moving toward the inner wall of the liquid container as described below.

For the device of the liquid surface cover for suppressing liquid force, as long as it is positioned so as to project beneath the liquid surface, thereby suppressing the force of the liquid moving toward the inner wall of the liquid container, there are no particular restrictions on its shape, location of installation, or the like. By way of a specific example, in addition to the side wall portion and the foot portion described above, a structure in which a fibrous matter (such as the hair on a brush, for example) is projected continuously in the circumferential direction without any substantial gaps may also be used.

Examples of the concavities and convexities provided on the side that makes contact with the inner wall of the liquid container include grooves, projections, and the like, and the arrangement thereof may be set up regularly at required intervals, or may also be set up irregularly (randomly).

An example of a means for adjusting the buoyancy of the float is, for instance, a float equipped with detachable buoyancy adjusters that produce buoyancy, wherein the number of the buoyancy adjusters is increased or decreased to adjust the buoyancy. In this case, the adjustment may be performed by using a plurality of identical buoyancy adjusters that produce the same amount of buoyancy, or by using more than one type of buoyancy adjusters that produce different amounts of buoyancy. Examples of the material of a buoyancy adjuster include synthetic resins such as polystyrene, synthetic resin foams such as polystyrene foam, polyethylene foam, polyvinyl chloride foam, and urethane foam, foam rubber, and the like.

The specific examples described above are only representative examples, and the present invention is not particularly limited to these.

While the present invention is described below with an embodiment, the present invention is not limited to this embodiment.

The present invention is described in further detail based on the embodiment shown in the drawings.

EMBODIMENT

FIG. 1 is an exploded perspective view showing an embodiment of a float of the present invention, and illustrates a float body and a buoyancy adjuster that is detachable from the float body.

Figure 2:
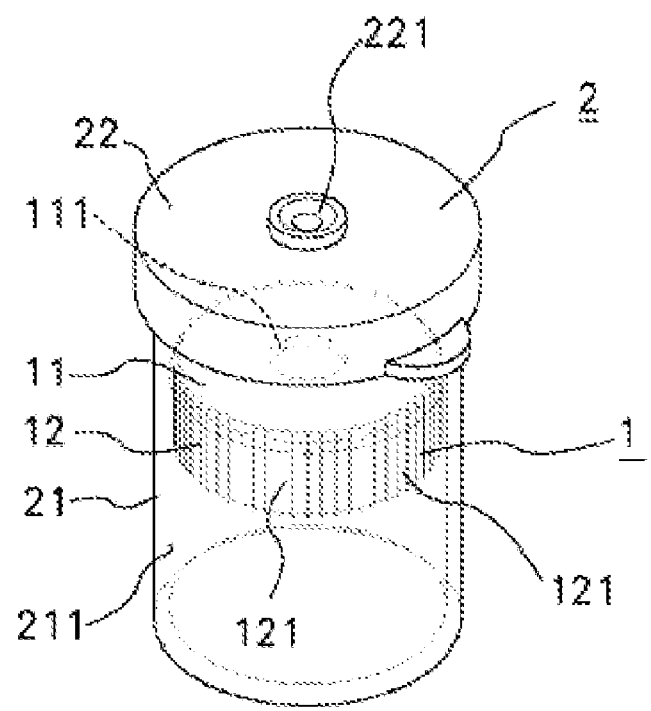
FIG. 2 is a perspective view showing a state in use of a reagent container provided with the float shown in FIG. 1.

FIG. 2 is a perspective view showing a state in use of a reagent container provided with the float shown in FIG. 1.

Figure 3:
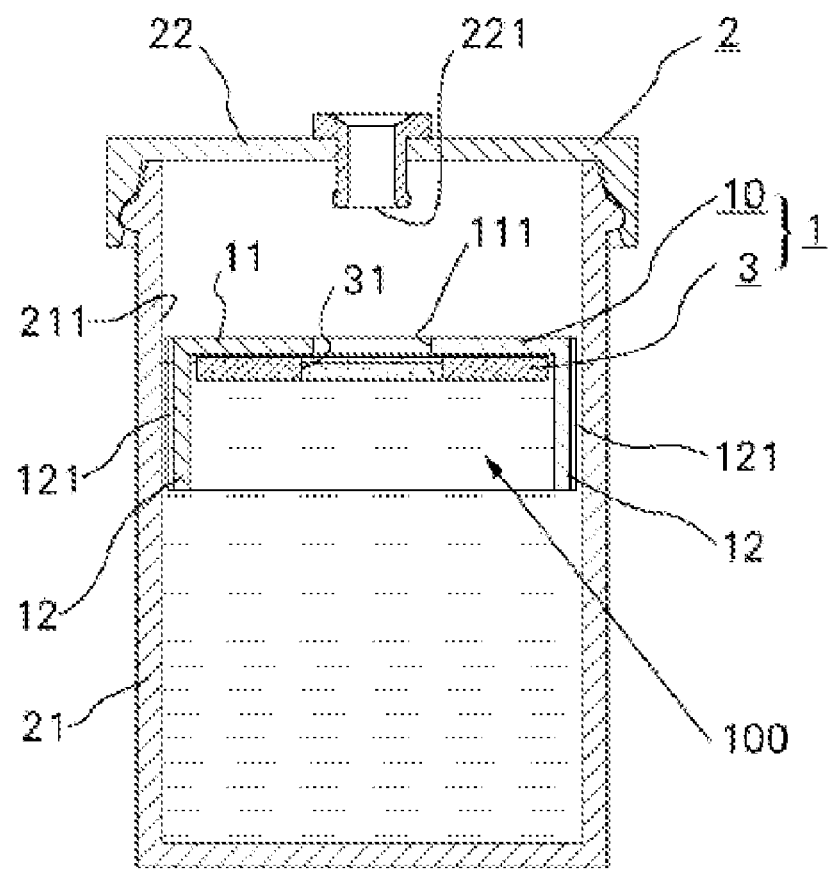
FIG. 3 is an explanatory drawing showing a vertical cross-section of FIG. 2.

FIG. 3 is an explanatory drawing showing a vertical cross section of FIG. 2.

The float 1 shown in FIG. 1 is to be used, as shown in FIG. 2, by floating it on a liquid (hereafter referred to as reagent) placed in a reagent container 2, which is a liquid container for use with an automatic analyzer. As described above (see FIG. 4), the reagent container 2 is used by mounting it onto a turntable 4, which is a movable mounting unit inside the automatic analyzer.

Reagent Container

First, the structure of the reagent container 2 is described with reference to FIGS. 2 and 3. Since the reagent container 2 is the same as a conventional one, the same reference numerals as assigned in FIGS. 4 and 5 will be used for the explanation.

In this embodiment, the reagent container 2 is provided with a bottomed, cylindrical container body 21 into which a reagent can be placed, and a cover 22 that closes the opening (reference numeral omitted) of the container body 21. The cover 22 is provided with a reagent collection opening 221, which is a liquid collection opening into which a probe for collecting reagent equipped with a liquid-level sensor can be inserted. The container body 21 possesses transparent characteristics so that the amount of reagent can be ascertained from the outside. The cover 22 is removed when replenishing the reagent.

Float

Next, the float 1 is described with reference to FIGS. 1 to 3.

As shown in FIG. 1, the float 1 is provided with a float body 10 and a required number of buoyancy adjusters 3 (see FIGS. 1 and 3) that can be attached detachably to the float body 10. The buoyancy of the float 1 can be adjusted by means of the buoyancy adjusters 3, but there are cases in which, depending on the specific gravity and viscosity of the reagent, it is not necessary to use the buoyancy adjusters 3, and in such a case, the float 1 is constituted only with the float body 10.

The float body 10 is made of a synthetic resin such as polypropylene and is formed into a circular shape as seen in a plan view. The float body 10 has a diameter that is slightly smaller than the inner diameter of the container body 21, and is designed to be able to move up and down in accordance with changes in the height of the liquid surface inside the container body 21. As a result, a liquid surface cover 11 is able to cover the liquid surface continuously.

As shown in FIG. 3, the float body 10 is formed into an approximate flattened C-shape in cross section, and is equipped with a liquid surface cover 11 composed of a top plate that covers substantially the entire liquid surface, and a side wall portion 12 positioned so as to project from the liquid surface cover 11 to beneath the liquid surface and provided continuously in the circumferential direction of the liquid surface cover 11. The side wall portion 12 constitutes a device for suppressing swaying motions that makes contact with or engages an inner wall 211 of the reagent container 2 when the liquid sways so as to suppress swaying motions of the liquid surface cover 11. The side wall portion 12 also functions as a device for suppressing liquid force for the purpose of suppressing the force of the liquid moving toward the inner wall 211 of the reagent container 2. The liquid surface cover 11 is provided with an opening 111 at the center portion thereof for the purpose of collecting the reagent with a probe.

The outer diameter of the float body 10 is preferably $8/10$ to $9.5/10$ of the inner diameter of the container body 21. If smaller than $8/10$ of the inner diameter of the container body 21, there is a risk that the float body 10 will become inverted, or that the reagent will move along the inner wall 211 to splash up through the gap between the float body 10 and the inner wall 211 of the container body 21, and therefore this is undesirable. Also, if larger than $9.5/10$ of the inner diameter of the container body 21, the float body 10 will become unable to move up and down smoothly in the container body 21, and removal of the float body 10 from the container body 21 will become troublesome, so this is also undesirable.

Furthermore, the height of the side wall portion 12 is preferably $3/10$ to $4.5/10$ of the inner diameter of the container body 21. If shorter than $3/10$ of the inner diameter of the container body 21, then depending on the size of the gap between the float body 10 and the inner wall 211, the liquid surface cover 11 becomes more easily swayed with respect to the inner wall 211, and this is undesirable. Also, even if taller than $4.5/10$ of the inner diameter of the container body 21, the effect of the side wall portion 12 of suppressing swaying motions does not change, but on the contrary, the height of the float body 10 becomes too tall, and when the amount of reagent becomes small, the float body 10 may make contact with the bottom of the container body 21 and the liquid surface may drop below the float body 10, so this is also undesirable.

The side wall portion 12 described above constitutes the side that makes contact with the inner wall 211 of the container body 21. The outer surface of the side wall portion 12 is provided with lengthwise grooves 121 along the circumferential direction of the inner wall 211 at required intervals to form concavities and convexities. These grooves 121 reduce the area of contact when the float body 10 and the inner wall 211 make contact, and are designed so that the float body 10 will move up and down smoothly in the container body 21 even if the outer diameter of the container body 21 is relatively large.

Also, even if the inner diameter of the float body 10 is relatively small, the reduction in contact area prevents the side wall portion 12 of the float body 10 from becoming stuck to the inner wall 211 of the container body 21, making it possible to prevent the float body 10 from swaying with respect to the inner wall 211.

The buoyancy adjuster 3 described above (see FIGS. 1 and 3) can be detachably attached to a concave portion 100 (see FIG. 3) of the float body 10 surrounded by the side wall portion 12. The buoyancy adjuster 3 is formed from a synthetic resin such as polystyrene or a synthetic resin foam such as polystyrene foam or urethane foam.

The buoyancy adjuster 3 is formed in the shape of a thin circular plate as seen in a plan view, and is provided with an opening 31 at the center portion thereof for the purpose of collecting the reagent with the probe, similarly to the float body 10. The outer diameter of the buoyancy adjuster 3 is slightly smaller than the inner diameter of the concave portion 100 of the float body 10. Moreover, the outer diameter of the buoyancy adjuster 3 can also be formed to be of the same size as or slightly larger than the inner diameter of the float body 10. In this way, by pushing the buoyancy adjuster 3 deep into the concave portion 100, a configuration can be realized in which the buoyancy adjuster 3 will not easily become dislodged from the float 1.

The buoyancy of the float 1 can be adjusted by increasing or decreasing the number of the buoyancy adjusters 3 attached to the float 1. Thus, even if the specific gravity and viscosity of the liquid stored in the reagent container 2 change, the buoyancy of the float 1 can be adjusted to an optimal state so that the float 1 does not sink beneath the liquid surface.

The float 1 of the present embodiment operates in the following manner.

Figure 4:
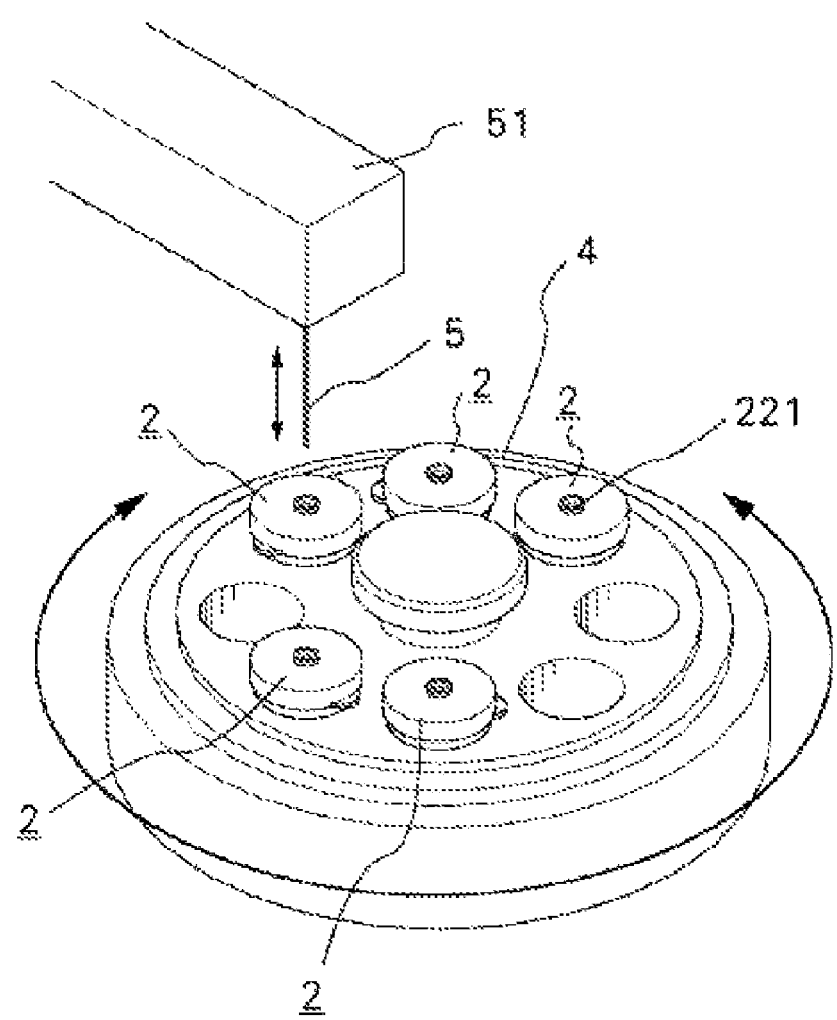
FIG. 4 is a schematic drawing for explaining a turntable and an arm equipped with a probe in an automatic analyzer.
Figure 5:
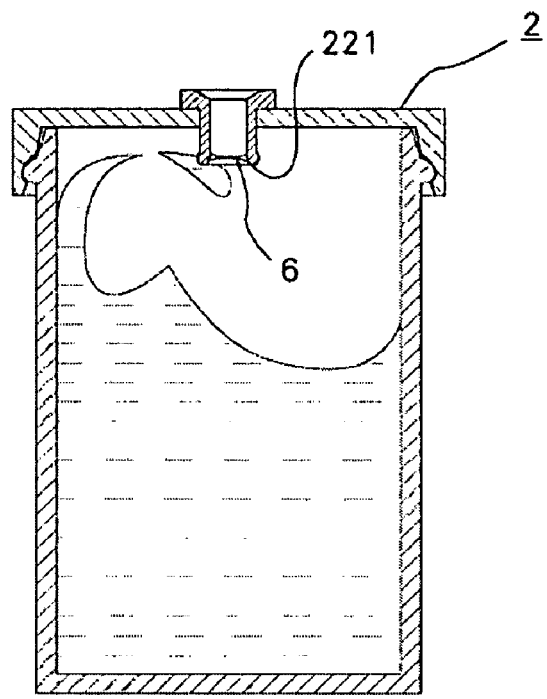
FIG. 5 is an explanatory drawing showing the state in which a reagent comes into contact with a reagent collection opening and forms a film in a reagent container.

Since the automatic analyzer that houses the reagent container 2 is the same as a conventional one, the explanation will refer to FIG. 4 and assign the same reference numerals as shown in FIG. 4.

As shown in FIGS. 2 and 3, the float body 10 is floated on the liquid surface of the reagent placed in the reagent container 2. If the float body 10 tends to sink beneath the liquid surface, a required number of buoyancy adjusters 3 are attached to the concave portion 100 of the float body 10 to adjust the buoyancy. In the present embodiment, a state is shown in which a single buoyancy adjuster 3 has been attached.

Floating the float 1 on the liquid surface enables the area of contact between the liquid surface and air to be reduced. As a result, deterioration of the reagent due to oxidation or the like can be prevented. The container body 21, after having a cover 22 attached thereon, is mounted onto the turntable 4 inside the automatic analyzer (see FIG. 4), and analysis is commenced.

The turntable 4 rotates so as to position a desired reagent container 2 directly underneath the probe 5. Then, the arm 51 lowers and the probe 5 is inserted through a reagent collection opening 221 of the reagent container 2. The probe 5 is inserted through the opening 111 of the float body 10 to beneath the liquid surface and collects the reagent. In the present embodiment, since the buoyancy adjuster 3 is attached to the float body 10, the probe 5 is also inserted through the opening 31 of the buoyancy adjuster 3 to beneath the liquid surface. After collection, the reagent is dispensed into a reaction container containing a blood test specimen, and an analysis is performed.

The reagent container 2 sways horizontally due to the rotation of the turntable, but the float 1 acts as described below to prevent the reagent from making contact with the reagent collection opening 221.

That is, even if the reagent container 2 sways horizontally, since the liquid surface cover 11 of the float body 10 covers substantially the entire liquid surface with its parts except the opening 111, swaying and tilting of the liquid surface are prevented or reduced.

Figure 6:
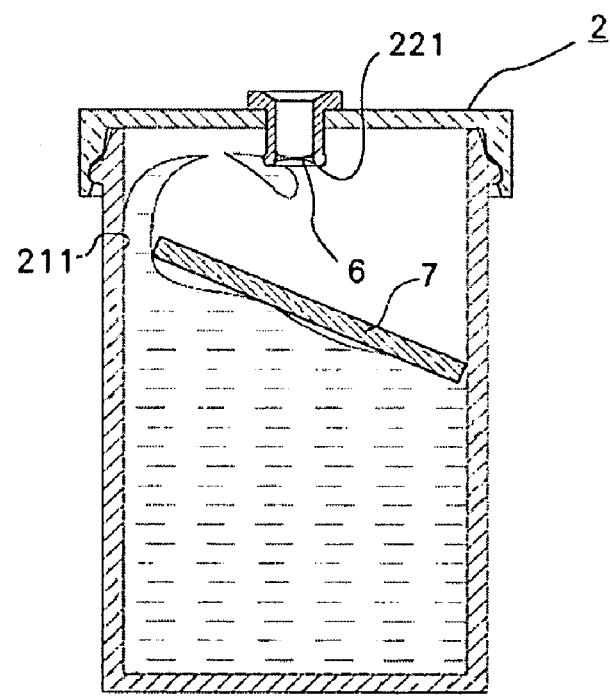
FIG. 6 is an explanatory drawing for the case in which a conventional solution stabilization member is used in the reagent container shown in FIG. 5.

Furthermore, differing from a conventional solution stabilization member 7 (see FIG. 6) that ends up tilting to the left and right together with the liquid surface when the reagent container 2 sways horizontally, in the present embodiment, the side wall portion 12 of the float 1 of the liquid surface cover 11 makes contact with the inner wall 211 of the reagent container 2 to suppress swaying motions of the liquid surface cover 11 with respect to the inner wall 211. This prevents the formation of a gap between the inner wall 211 and the liquid surface cover 11, through which the reagent that collides with the inner wall 211 may splash up. Thus, it is possible to prevent the reagent from making contact with the reagent collection opening 221 of the reagent container 2 to form a film.

As a result, as described above, the probe 5 equipped with a liquid-level sensor is inserted through the reagent collection opening 221 of the reagent container 2 to beneath the liquid surface and reliably collects the reagent without malfunctioning. Thus, it is possible to prevent the occurrence of incorrect examination results due to malfunction of the probe 5.

Moreover, the side wall portion 12 has an effect of suppressing swaying motions on the float 1 as described above and also an effect of suppressing the force of liquid (reagent) that moves toward the inner wall 211 of the reagent container 2. That is, even if horizontal swaying of the reagent container 2 causes the reagent to move toward the inner wall 211, the side wall portion 12, positioned so as to project from the liquid surface cover 11 to below the liquid surface, suppresses the flow of the reagent, thereby suppressing the force of the reagent moving toward the inner wall 211. This makes it possible to prevent the reagent from forcefully colliding with the inner wall 211 to splash up.

The terminology and expressions used in the present specification are for explanatory purposes only and are not limitative, and terminology and expressions equivalent to the terminology and expressions mentioned above are not excluded. Moreover, the present invention is not limited to the embodiment illustrated, and various modifications are possible within the scope of the technical ideas.

Furthermore, the scope of the patent claims is not limited to the elements described in the drawings.

According to the present invention, even in cases in which the liquid container sways horizontally, for example, the device of the float for suppressing swaying motions makes contact with or engages the inner wall of the liquid container, thereby suppressing swaying motions of the liquid surface cover that covers substantially the entire liquid surface. Accordingly, the formation of a gap between the inner wall and the liquid surface cover, through which liquid may move along the inner wall to splash up, is prevented. Thus, it is possible to prevent the liquid from making contact with the liquid collection opening of the liquid container to form a film. Consequently, it is possible to prevent the occurrence of incorrect examination results due to malfunction of a probe equipped with a liquid-level sensor.

Also, according to the present invention, even in cases in which the liquid container sways horizontally, for example, a device of the float for suppressing liquid force, positioned so as to project beneath the liquid surface, suppresses the force of the liquid moving toward the inner wall of the liquid container. This makes it possible to prevent the liquid from forcefully colliding with the inner wall to splash up. Thus, similarly to the matter described above, the liquid is prevented from making contact with the liquid collection opening of the liquid container to form a film, and it is possible to prevent the occurrence of incorrect examination results due to malfunction of a probe equipped with a liquid-level sensor.

For a float provided with concavities and convexities on the side that makes contact with the inner wall of the liquid container, the area of contact in cases in which the float and the inner wall make contact can be reduced. As a result, the float is able to move up and down smoothly in accordance with changes in the height of the liquid surface, and the liquid surface can be covered continuously with the liquid surface cover. Also, the reduction of contact area prevents the float from becoming stuck to the inner wall of the container body, thereby making it possible to prevent swaying motions of the float with respect to the inner wall.

For a float provided with a means for adjusting buoyancy, even if the specific gravity and viscosity of the liquid stored in the liquid container change, the buoyancy of the float can be adjusted to an optimal state so that the float does not sink beneath the liquid surface.

According to a method for preventing malfunction of a probe in an automatic analyzer and an examination method that uses an automatic analyzer, as a result of the effects of the float described above, malfunction of a probe equipped with a liquid-level sensor is prevented, thereby making it possible to prevent the automatic analyzer from yielding incorrect examination results.

The invention claimed is:

1. A float for the purpose of floating on a liquid placed in a liquid container for use with an automatic analyzer, the float comprising:
a liquid surface cover covering substantially the entire liquid surface and comprising an opening for the purpose of collecting the liquid;
a swaying-motion-suppressing device that at least one of contacts or engages an inner wall of the liquid container when the liquid sways so as to suppress swaying motions of the liquid surface cover; and
wherein the swaying-motion-suppressing device comprises concavities and convexities on a side that makes contact with the inner wall of the liquid container.

2. The float as described in claim 1, further comprising a buoyancy-adjusting device.

3. An apparatus comprising the float and the liquid container as described in claim 2.

4. A method for preventing malfunction of a probe equipped with a liquid-level sensor in an automatic analyzer wherein a film formed on a liquid collection opening of a liquid container is mistakenly detected as the surface of a liquid, the method comprising the step of floating the float as described in claim 2 on the liquid in the liquid container to prevent the liquid from making contact with the liquid collection opening so that a film is not formed.

5. An examination method using an automatic analyzer that collects liquid stored in a liquid container provided on a movable mounting unit by means of a probe equipped with a liquid-level sensor, and performs analyses, the examination method comprising the step of floating the float as described in claim 2 on the liquid in the liquid container to perform an examination in a state in which the liquid is prevented from making contact with a liquid collection opening of the liquid container.

6. An apparatus comprising the float and the liquid container as described in claim 1.

7. The float as described in claim 1, further comprising a buoyancy-adjusting device.

8. A method for preventing malfunction of a probe equipped with a liquid-level sensor in an automatic analyzer wherein a film formed on a liquid collection opening of a liquid container is mistakenly detected as the surface of a liquid, the method comprising the step of floating the float as described in claim 1 on the liquid in the liquid container to prevent the liquid from making contact with the liquid collection opening so that a film is not formed.

9. An examination method using an automatic analyzer that collects liquid stored in a liquid container provided on a movable mounting unit by means of a probe equipped with a liquid-level sensor, and performs analyses, the examination method comprising the step of floating the float as described in claim 1 on the liquid in the liquid container to perform an examination in a state in which the liquid is prevented from making contact with a liquid collection opening of the liquid container.

10. A float for the purpose of floating on a liquid placed in a liquid container for use with an automatic analyzer, the float comprising:
a liquid surface cover covering substantially the entire liquid surface and comprising an opening for the purpose of collecting the liquid;
a liquid-force-suppressing device positioned so as to project beneath the liquid surface and constituted so as to suppress the force of the liquid that moves toward an inner wall of the liquid container when the liquid sways; and
wherein the liquid-force-suppressing device comprises concavities and convexities on a side that makes contact with the inner wall of the liquid container.

11. The float as described in claim 10, further comprising a buoyancy-adjusting device.

12. An apparatus comprising the float and the liquid container as described in claim 11.

13. An apparatus comprising the float and the liquid container as described in claim 10.

14. A method for preventing malfunction of a probe equipped with a liquid-level sensor in an automatic analyzer wherein a film formed on a liquid collection opening of a liquid container is mistakenly detected as the surface of a liquid, the method comprising the step of floating the float as described in claim 10 on the liquid in the liquid container to prevent the liquid from making contact with the liquid collection opening so that a film is not formed.

15. An examination method using an automatic analyzer that collects liquid stored in a liquid container provided on a movable mounting unit by means of a probe equipped with a liquid-level sensor, and performs analyses, the examination method comprising the step of floating the float as described in claim 10 on the liquid in the liquid container to perform an examination in a state in which the liquid is prevented from making contact with a liquid collection opening of the liquid container.

* * * * *